Figure 2:
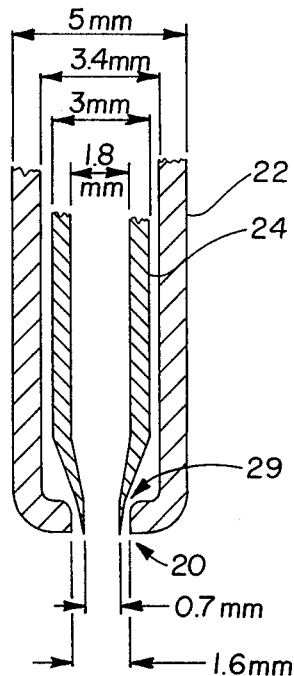

United States Patent [19]

Van Sickle et al.

[11] Patent Number: 4,468,356

[45] Date of Patent: Aug. 28, 1984

[54] DIKETENE CHLORINATION METHOD

[75] Inventors: Dale E. Van Sickle; Gordon C. Newland; Jeffrey J. Siirola; Steven L. Cook, all of Kingsport, Tenn.

[73] Assignee: Eastman Kodak Company, Rochester, N.Y.

[21] Appl. No.: 436,540

[22] Filed: Oct. 25, 1982

Related U.S. Application Data

[63] Continuation-in-part of Ser. No. 254,248, Apr. 15, 1981, abandoned.

[51] Int. Cl.$^3$ .................. C07C 51/58; C07C 67/46
[52] U.S. Cl. ...................... 260/544 Y; 560/174; 260/694
[58] Field of Search .............. 260/544 Y, 694; 570/101; 560/174

[56] References Cited

U.S. PATENT DOCUMENTS

| | | | |
|---|---|---|---|
| 2,031,938 | 2/1936 | Deanesly et al. | 260/694 |
| 2,209,683 | 7/1940 | Boese, Jr. | 260/544 Y |
| 2,643,272 | 6/1953 | Lacomble et al. | 260/694 |
| 2,765,353 | 10/1956 | Neher | 260/694 |
| 3,666,793 | 5/1972 | Stocker et al. | 260/544 Y |

*Primary Examiner*—Natalie Trousof
*Assistant Examiner*—L. Hendriksen
*Attorney, Agent, or Firm*—Donald W. Spurrell; Daniel B. Reece, III

[57] ABSTRACT

Disclosed is a process and apparatus for the chlorination of diketene, by contacting the diketene in nebulized form with chlorine gas, which contacting can be in the absence of a solvent or diluent, in an essentially uncooled reaction zone of short residence time followed by a cooling zone wherein at least a portion of the heat of reaction is removed from the product without the need for refrigeration.

6 Claims, 2 Drawing Figures

DIKETENE CHLORINATION METHOD

DESCRIPTION

This is a continuation-in-part application of Ser. No. 254,248, filed Apr. 15, 1981, now abandoned.

This invention concerns the chlorination of diketene, and in the preferred embodiment concerns a relatively high rate, non-solvent, non-refrigerated continuous process and apparatus for carrying out the chlorination.

Heretofore, the recommended chlorination procedures in the art specify, in the case of diketene, that the highly exothermic chlorination be done at moderate to high dilution, usually in an inert, chlorinated solvent, and sometimes with an inert gas diluent for the chlorine, and that both the chlorination and subsequent esterification to the 4-chloroacetoacetic acid ester be done at low temperatures. See for example, U.S. Pat. 3,666,793 wherein in order to maximize selectivity to the desired 4-chloroacetoacetyl chloride intermediate (4-CAAC) rather than, for example, 2,4-dichloroacetoacetyl chloride or 2-chloroacetoacetyl chloride, it is taught that chlorine gas should be added slowly to a batch of diketene diluted with an inert, low boiling solvent such as methylene chloride, carbon tetrachloride, dichloroethane, or liquid sulfur dioxide, and that the heat of both chlorination and esterification be removed by refrigeration to maintain the batch temperature within $-10°$ C. to $-30°$ C. In an alternative process of Japanese Pat. No. 76,113,824 employing a continuous, descending stream, wetted-wall column reactor, diketene in dichloroethane and chlorine diluted with nitrogen were reacted at $10°$ C. and the product esterified at $-5°$ C. With such prior processes, the need for refrigeration and diluents and the separation thereof from the product and their disposal or recovery impose onerous economic penalties on the production of the desired 4-chloroacetoacetic acid ester.

In accordance with the present invention, however, it has been discovered that 4-chloroacetoacetyl chloride from diketene, can be produced continuously in high yield without the use of diluents and refrigeration by carrying out the chlorination in a certain way in a special apparatus shown in detail in the accompanying drawing. The invention, in its broad sense, is defined as a process for the continuous chlorination of diketene, comprising continuously nebulizing said diketene within a reactor, continuously contacting the spray with chlorine gas in an essentially uncooled reaction zone, directing the resultant reaction system against a cooled reactor wall, and continuously removing liquid product from said reactor. It is noted that in this process at least a major portion of the reaction, and usually essentially all of the reaction has taken place before the spray contacts the reactor wall. The cooled wall in the present process acts only to provide a condensing and run-off surface for the chlorinated product which in the absence of a limited size spray reaction zone might degrade, polymerize or become overchlorinated due to the very high temperatures within the reaction zone and the continued intimate contact of the 4-CAAC product and $Cl_2$ gas. It is noted that the yields of desired product produced according to the present invention are significantly improved over that obtained with wetted wall reactors wherein overchlorination and degradation or polymerization occurs.

Figure 1:
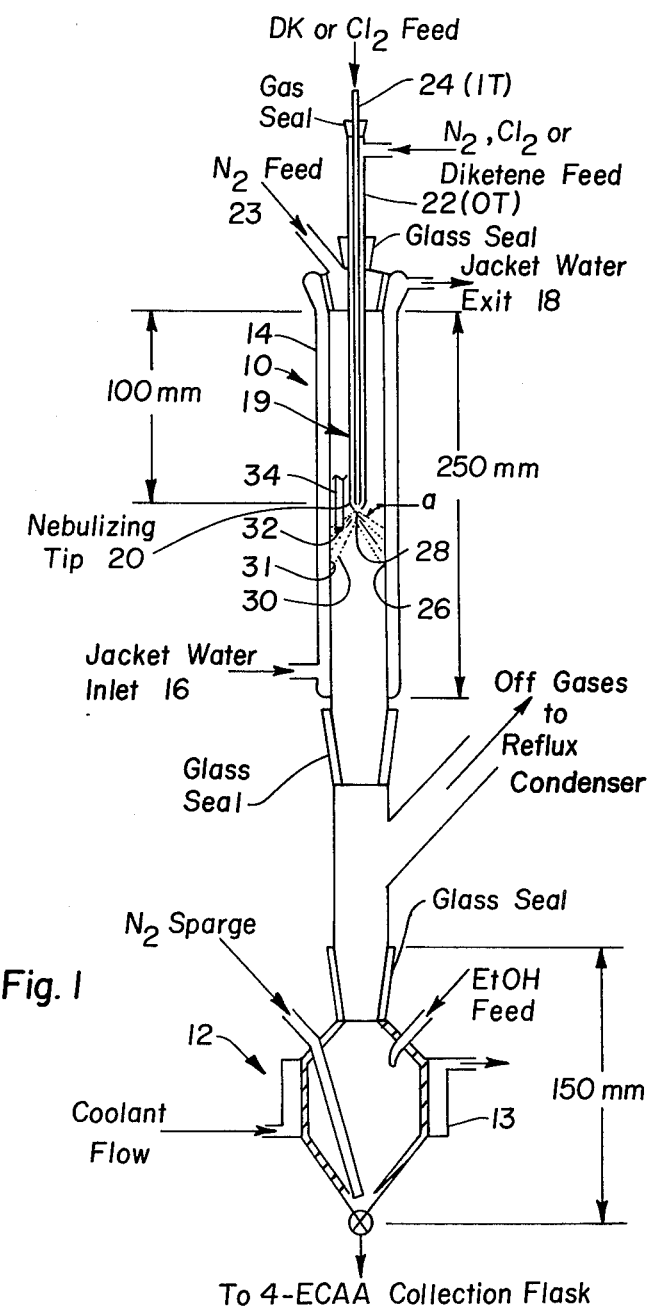

The invention will be further understood from the following description and drawing wherein:

FIG. 1 is a partially schematic and cross-sectional view of the chlorinator and sub-joined esterification unit; and FIG. 2 is a cross-sectional view of the tip portion of an actual nebulizer with dimensions, with which chlorinations were carried out in a column of about 10.0 mm inside diameter.

Referring to the drawing, the apparatus is shown as consisting of a column chlorinator generally designated 10 and an esterification reactor generally designated 12. The chlorinator is preferably provided with a fluid cooling jacket 14 having a suitable fluid inlet 16 and outlet 18 for continuous and controlled flow of cooling fluid, preferably water. The chlorinator is sealed at the top and provided in its upper portion with an atomizer or nebulizer 19 which may be any of a large variety of constructions including internal and external mixing types as shown, for example, in Industrial Catalog 26 of Spraying Systems Co., Wheaton, Ill. of either the single or double fluid type. The nozzle or tip 20 may be of any configuration and dimensions known to the art as long as it is capable of nebulizing diketene by itself or with chlorine gas or other gas such as nitrogen, over a wide range of reactant feed rates such that the chlorination rate, column temperature and the like may be controlled, at least to some extent by varying the rates of diketene feed. Where a non-reactant gas is used to nebulize the diketene, the chlorine may be fed through port 23.

The nebulizer 19, in the embodiment shown in the drawing, comprises outer tube (OT) 22, inner tube (IT) 24 concentric therewith, and tip 20, the outer tube being spaced from the chlorinator wall (CW) 26, a sufficient distance to allow proper nebulization and contact of the diketene with the chlorine before striking the reactor wall. In commercial scale apparatus employing high reactant feed rates, high nebulizing pressures and the like, the relative dimensions and configurations of the various structural components can be varied greatly according to established chemical engineering principles within the general requisite of the present invention that substantial, concurrent mixing and reacting of the diketene and chlorine occur within the nebulized reaction system indicated by dotted lines 30 being directed against the cooled, reaction system condensation surface 31 of the chlorinator wall 26. The diameters of the above structural elements at the tip are such that the space between CW and OT is about 5 mm., and between OT and IT is about 0.4 mm., and the lengths of OT and IT need only be such as to provide a directional flow pattern of each reactant which can effect an adequate spray pattern at the nebulizer tip outlet 28. Condensation surface 31 must be sufficiently upstream of the exhaust end to allow adequate residence time for liquification of the reaction system or product impinging thereon. The gap 29 in FIG. 2 is about 0.4 mm wide. The actual dimensional proportions shown in the drawing represent an operable apparatus which may be scaled up by those skilled in the art to give the desired production rates. Specific, useful commercial spray devices are shown, for example, in Industrial Catalog 27, copyright 1978, Spraying Systems Co., Wheaton, Ill., as exemplified by ¼ JBC nozzle on page 47 thereof, and having the cross-section and flat spray pattern as shown on page 51, ibid.

The present chlorination apparatus is broadly defined as comprising an elongated column having a reactant feed end and a product exhaust end, and a nebulizer in said column adapted for connection to exterior feeds of organic material and nebulizing gas, the outlet of said nebulizer being positioned within said column upstream of said product exhaust end to provide a reaction system condensation surface on said column wall upstream of said exhaust end.

In carrying out the process, the chlorine and diketene, are introduced concurrently and continuously into the top of the chlorinator. The terms "continuous" and "continuously" as used herein are intended to contrast the present process with a batch process, and not to imply that the present process is limited only to greatly extended run periods. Bulk stoichiometry is controlled by reactant flow control. The preferred molar feed rate ratio of $Cl_2$ to diketene is 1.0, but a wide ratio range is operable, e.g., 0.1 to 10, with from about 0.5 to about 1.5 being preferred. Specific feed rates for the reactants in an apparatus dimensioned as shown in the drawing are given in the table below. Particularly effective rates are about 0.042 gm moles per minute of diketene into tube 24 and about 0.047 gm moles of chlorine per minute into tube 22 with a temperature of about 78° C. for the off gases and acyl chloride product, and a jacket water temperature of about 22° C. It is noted that the feed ratio may be adjusted to favor the production of one chlorinated product over another in those instances where various by-products are possible. This is possible with the present invention since the reaction occurs within the spray and the reactants can thus be carefully metered to the nebulizer, avoiding overloading the reactor with an excess of $Cl_2$. The heat of reaction is removed and the product is condensed by heat transfer through the walls of the chlorinator to the surrounding jacket 14 containing cooling fluid within the range of, for example, from about 0° C. or lower to about 50° C. or higher, and preferably from about 18° C. to about 30° C. The actual temperature of the chlorinator inner wall (condensation surface) ranges, of course, between the temperatures of the aforesaid reaction zone and cooling fluid, and can range, for example, from about −15° C. to 100° C., preferably from about 15° C. to about 50° C. It is particularly noted that since in the present process the reaction takes place away from said condensation surface at such high temperatures of from about 80° C. to about 210° C., it is preferable to move the product as quickly as possible out of the reactor and into the esterification unit, and also to cool the product as quickly as possible in order to prevent overchlorination and/or resin formation. A low coolant temperature which can range down to several degrees below zero, e.g. −20° C., can be employed to advantage therefore; however, the temperature of river water and the convenience in the use thereof is preferable. Neither the diketene nor the chlorine needs to be diluted, although a small inert gas purge may be introduced into the bottom of the chlorinator column to maintain pressure as the chlorine gas is reacted, and to limit entry into the chlorinator of hydrogen chloride by-product produced in the subjoining esterification reactor 12.

The acid chloride product which is relatively unstable is condensed on the walls of the chlorinator and then accumulates and flows continuously to the agitated reactor 12 in which alcohol is also continuously added. A cooling jacket 13 may be provided around this reactor to prevent undue temperature build-up. An agitator is provided at any convenient location in the reactor in known manner. In practice, it is preferable that the hydrogen chloride liberated during the esterification be passed through a condenser for excess ethanol recovery and then to a scrubber for recovery or disposal. The product ester such as methyl or ethyl-4-chloroacetoacetate (4-ECAA), is continuously removed from the reactor 12 for purification and/or processing into other compounds of interest such as quinacridone pigments, by procedures known in the art as described in the article of M. Sommelet and P. Cauroux, Bull. Soc. Chim. Fr., 29, 402 (1921) in the conversion of 4-MCAA to dimethyl-2,5-dioxo-1,4-cyclohexane-1,4-dicarboxylate which is convertible to quinacridone pigment as described on page 858 of Encyclopedia of Chemical Technology, Kirk-Othmer, 3rd Ed., Vol 17. Residence time in the esterification reactor is conveniently adjusted by liquid level control.

In the case of diketene, good selectivity to the desired 4-chloroacetoacetyl chloride can be achieved by careful control of diketene and chlorine feed (stoichiometry), rather than through the difficult procedure of maintaining efficient but low chlorination temperatures. In this regard, a large excess of chlorine is detrimental in this particular reaction as it reacts with the desired product to form 2,4-dichloroacetoacetyl chloride and hydrogen chloride, while an excess of diketene gives acetoacetic acid esters. Back-mixing may also be detrimental in causing excessive chlorination of the product and reaction of hydrogen chloride with diketene to give unwanted by-products. Optimum yields of the desired product are obtained with a slight excess of chlorine, with the reaction system directed continuously against the cooled reactor column wall, and with continuous withdrawal of product.

The reaction between diketene and chlorine appears to be limited only by mass transfer at the diketenechlorine interface. The temperature within the reaction zone depends upon the reaction rate and hence on the interfacial area, and consequently can be sufficiently high in a particular chlorinator to require heat removal, as aforesaid, through the walls of the chlorinator to the cooling jacket. In the present process the spray reaction zone temperature is the temperature of the spray or actual site of reaction, as measured approximately at the midpoint of the outer edge of the nebulizer tip 20 to the condensation surface 31 along the line of spray which typically is about at a 45° angle ($\alpha$) with respect to the reactor wall, but which angle, of course, will change with changes in reactant feed pressures and/or rates of flow. As shown in the drawing the tip 32 of the temperature measuring device 34 is set at approximately the center of the conical spray pattern. This device is conveniently inserted through port 23 and sealed therein during the temperature measuring period. This temperature ranges from about 80° C. to about 210° C., preferably from about 100° C. to about 170° C., and most preferably from about 120° C. to about 160° C., which temperatures, according to the prior art are much too high for successful chlorination of diketene to 4-chloroacetoacetyl chloride. The product temperature is preferably no higher than about 100° C. coming from the chlorinator with a preferred residence time therein of from about 1 to about 10 seconds. As the product is not stable, it is important to remove the heat of reaction as quickly as possible, although we have discovered that neither temperature moderation through the use of a diketene solvent or a chlorine diluent, nor the use of a refrigerated cooling media for the reaction zone is necessary, particularly if stoichiometry is carefully controlled. The warm acid chloride product is immediately esterified in the continuous reactor 12 and this reaction is mildly exothermic requiring jacket type cooling but not refrigeration. The esterification reaction is slower than the chlorination and both excess alcohol and back-mixing are tolerable but not preferred.

The following table gives a series of diketene chlorination runs in apparatus such as shown in the drawing. The jacket temperature for the first two runs 1 and 2 was maintained at 5°–15° C. with refrigerated water. Subsequently, water at 22° C. was employed for cooling with no apparent effect on the reaction. In some of the runs, the temperature of the exhaust gases and acyl chloride product was measured in the space below the areas jacketed by 14 and the off-gases take off. The temperature ranged from 35° C. for run 10, which was performed at a low through-put rate, to 78° C. for run 11 which was made at a high through-put rate. Comparison of runs 9, 10, and 11 indicates that changing through-put rate had only little effect on 4-ECAA yield. Runs 3, 4, 5, and 6 wherein the ratio of diketene to chlorine reacted was progressively lowered, show that under- and overchlorinated product is obtained in all cases. The last four runs of the table, 12, 13, 14 and 15, were performed with chlorine as the nebulizing gas.

The invention has been described in detail with particular reference to preferred embodiments thereof, but it will be understood that variations and modifications can be effected within the spirit and scope of the invention.

We claim:

1. In a process for the continuous chlorination of diketene, the improvement of continuously nebulizing said diketene within a reactor, continuously contacting the diketene spray with chlorine gas in a reaction zone consisting essentially of the chlorine gas, diketene and reaction product, at a temperature of from 80° C. to about 210° C., directing the resultant reaction system and product against a condensation surface, and continuously removing liquid product from said reactor.

2. The process of claim 1 wherein the molar ratio of diketene feed to chlorine is from about 0.5 to about 1.5.

3. The process of claim 2 wherein the chlorinated product is fed directly to an esterification unit wherein the temperature is maintained within the range of from about 15° C. to about 40° C.

4. The process of claim 1 wherein the temperature within said reaction zone is from about 100° C. to about 170° C.

5. The process of claim 1 wherein the temperature within said reaction zone is from about 120° C. to about 160° C.

6. The process of claim 1 wherein the temperature of said condensation surface is between about 15° C. and about 50° C.

Chlorination of Diketene (DK) in the Spray/Wetted Wall Reactor And Ethanolysis of Product to Ethyl 4-Chloroacetoacetate (4-ECAA)

| Run No. | Reactants, Moles[a] | | | Product, Moles[b] | | | | | Yield[c] |
| --- | --- | --- | --- | --- | --- | --- | --- | --- | --- |
|  | DK | Cl2 | EtOH | 4-ECAA | EAA | 2,4-EDAA | Other Vol. | 2-ECAA | 4-ECAA, % |
| 1[d]  | 0.580 | 0.661 | 0.794 | 0.445 | 0.022 | 0.063 | 0.010 | — | 76.7 |
| 2[e]  | 0.551 | 0.619 | 0.803 | 0.404 | 0.014 | 0.064 | 0.013 | — | 73.3 |
| 3  | 0.580 | 0.394 | 0.846 | 0.324 | 0.199 | 0.021 | 0.027 | 0.001 | 55.8 |
| 4  | 0.602 | 0.506 | 0.870 | 0.385 | 0.113 | 0.031 | 0.035 | 0.002 | 63.9 |
| 5  | 0.604 | 0.591 | 0.894 | 0.412 | 0.057 | 0.055 | 0.025 | 0.009 | 68.2 |
| 6  | 0.592 | 0.639 | 0.900 | 0.422 | 0.026 | 0.070 | 0.041 | 0. | 71.3 |
| 7  | 0.572 | 0.601 | 0.829 | 0.418 | 0.040 | 0.054 | 0.034 | 0.001 | 73.1 |
| 8  | 0.598 | 0.608 | 0.918 | 0.439 | 0.029 | 0.056 | 0.033 | 0.001 | 73.4 |
| 9  | 0.554 | 0.627 | 0.888 | 0.424 | 0.026 | 0.064 | 0.038 | 0.001 | 76.5 |
| 10[f]  | 0.558 | 0.547 | 0.859 | 0.409 | 0.042 | 0.048 | 0.034 | 0.001 | 73.3 |
| 11[g]  | 0.051 | 0.612 | 0.890 | 0.428 | 0.016 | 0.069 | 0.032 | 0.001 | 77.7 |
| 12  | 0.597 | 0.773 | 0.911 | 0.398 | 0.009 | 0.109 | 0.037 | 0.002 | 66.7 |
| 13  | 0.587 | 0.667 | 0.879 | 0.406 | 0.020 | 0.070 | 0.022 | 0.001 | 69.2 |
| 14  | 0.566 | 0.566 | 0.865 | 0.419 | 0.035 | 0.029 | 0.019 | 0.001 | 74.0 |
| 15  | 0.545 | 0.566 | 0.806 | 0.360 | 0.037 | 0.047 | 0.026 | 0.002 | 66.1 |

[a] Delivered to the reactor over 16–20 minutes unless otherwise footnoted.
[b] 4-ECAA = Ethyl 4-chloroacetoacetate; EAA = Ethyl acetoacetate; 2,4-EDAA = Ethyl 2,4-dichloroacetoacetate; 2-ECAA = Ethyl 2-chloroacetoacetate; Other Vol. = sum of remaining unidentified volatiles in trace amounts, assuming a mole weight of 180.
[c] On DK consumed.
[d] 90 minute run.
[e] 40 minute run.
[f] 26.6 minute run.
[g] 13.3 minute run.

* * * * *